US 6,599,231 B1

(54) LOADING CLIP FOR RADIOISOTOPE SEEDS

(75) Inventors: Daniel M. Elliott, Shorewood, MN (US); George M. Hoedeman, Eden Prairie, MN (US); John J. Berkey, St. Louis Park, MN (US); Jonathan D. Elliott, St. Paul, MN (US)

(73) Assignee: Mentor Corporation, Santa Barabara, CA (US)

( * ) Notice: Subject to any disclaimer, the term of this patent is extended or adjusted under 35 U.S.C. 154(b) by 0 days.

(21) Appl. No.: 09/658,636

(22) Filed: Sep. 11, 2000

Related U.S. Application Data

(62) Division of application No. 09/587,642, filed on Jun. 5, 2000.

(51) Int. Cl.$^7$ .............................................. A61M 36/12
(52) U.S. Cl. ........................................................ 600/7
(58) Field of Search .................................. 600/1–8, 427; 604/57, 59–64; 250/507.1; 976/DIG. 350; 42/87, 88

(56) References Cited

U.S. PATENT DOCUMENTS

| | | | |
|---|---|---|---|
| 4,086,914 A | 5/1978 | Moore | |
| 4,150,298 A | 4/1979 | Brault et al. | |
| 4,167,179 A | 9/1979 | Kirsch | |
| 4,401,108 A | 8/1983 | Galkin | |
| 4,488,371 A | * 12/1984 | Boyles | ............................ 42/90 |
| 4,586,490 A | 5/1986 | Katz | |
| 4,627,420 A | 12/1986 | Katz | |
| 4,649,925 A | 3/1987 | Dow | |
| 4,673,813 A | 6/1987 | Sanchez | |

(List continued on next page.)

FOREIGN PATENT DOCUMENTS

| | | |
|---|---|---|
| EP | 1 070 519 | 1/2001 |
| GB | 1308041 | 2/1973 |
| WO | WO 97/22379 | 6/1997 |
| WO | WO 99/56825 | 11/1999 |
| WO | WO 99/60921 | 12/1999 |
| WO | WO 00/48664 | 8/2000 |
| WO | WO 00/61229 | 10/2000 |

OTHER PUBLICATIONS

Website print–out: *Indigo Express Seeding Cartridge*, Dec. 1999.

(List continued on next page.)

*Primary Examiner*—Max F. Hindenburg
*Assistant Examiner*—Joseph A. Cadugan
(74) *Attorney, Agent, or Firm*—Patterson, Thuente, Skaar & Christensen, P.A.

(57) ABSTRACT

A loading clip for low dose radioisotope seeds has a body having a channel defined therein. The channel has a cavity adapted for receiving a radioisotope seed at a distal end. A slider member slidably positionable within the channel has a spring biased tooth at a distal end. A constant force spring member is slidably positioned within the channel between the slider member and the body. Radioisotope seeds are magazined into the loading clip biased against the constant force spring member by operation of the slider member extending the tooth over the cavity and retracting a radioisotope seed in the cavity into the channel. In one embodiment, radioisotope seeds are magazined into the loading clip that is then used to load an automated seed cartridge. In this embodiment, the loading clip has structure for mating with an aperture in the automated seed cartridge so as to introduce radioisotope seeds into the seed cartridge one at a time. Preferably, the loading clip is provided with a machine readable storage medium accessible via an electrical connector that stores indicia representing at least information about the radioisotope seeds located in the loading clip.

8 Claims, 13 Drawing Sheets

U.S. PATENT DOCUMENTS

| | | | |
|---|---|---|---|
| 4,702,228 A | | 10/1987 | Russell, Jr. et al. |
| 4,719,715 A | * | 1/1988 | Howard .................. 42/87 |
| 4,759,345 A | | 7/1988 | Mistry |
| 4,763,642 A | | 8/1988 | Horowitz |
| 4,815,449 A | | 3/1989 | Horowitz |
| 4,851,694 A | | 7/1989 | Rague |
| 4,869,299 A | | 9/1989 | Handke |
| 4,881,937 A | | 11/1989 | Van't Hooft |
| 4,994,028 A | | 2/1991 | Leonard et al. |
| 5,030,194 A | | 7/1991 | Van't Hooft |
| 5,084,001 A | | 1/1992 | Van't Hooft |
| 5,092,834 A | | 3/1992 | Bradshaw |
| 5,103,395 A | | 4/1992 | Spako |
| 5,120,973 A | | 6/1992 | Rohe |
| 5,139,473 A | | 8/1992 | Bradshaw et al. |
| 5,147,282 A | | 9/1992 | Kan |
| 5,181,514 A | | 1/1993 | Solomon |
| 5,183,455 A | | 2/1993 | Hayman |
| 5,205,289 A | | 4/1993 | Hardy et al. |
| 5,242,373 A | | 9/1993 | Scott et al. |
| 5,272,349 A | | 12/1993 | Perry |
| 5,282,472 A | | 2/1994 | Companion |
| 5,355,606 A | * | 10/1994 | Origoni .................. 42/87 |
| 5,361,768 A | | 11/1994 | Webler |
| 5,377,436 A | * | 1/1995 | Switzer .................. 42/87 |
| 5,391,139 A | | 2/1995 | Edmundson |
| 5,415,169 A | | 5/1995 | Siczek |
| 5,460,592 A | | 10/1995 | Langton et al. |
| 5,470,008 A | * | 11/1995 | Rodak .................. 227/176.1 |
| 5,522,797 A | * | 6/1996 | Grimm .................. 604/61 |
| 5,540,649 A | | 7/1996 | Bonnell |
| 5,552,645 A | | 9/1996 | Weng |
| 5,626,829 A | | 5/1997 | Kourtrouvelis |
| 5,682,892 A | | 11/1997 | Selder |
| 5,695,500 A | | 12/1997 | Taylor |
| 5,713,828 A | | 2/1998 | Coniglione |
| 5,800,333 A | | 9/1998 | Liprie |
| 5,830,219 A | | 11/1998 | Bird |
| 5,833,627 A | | 11/1998 | Schmulewitz |
| 5,834,788 A | | 11/1998 | Fu et al. |
| 5,851,172 A | | 12/1998 | Bueche et al. |
| 5,851,173 A | | 12/1998 | Dugan |
| 5,860,909 A | | 1/1999 | Mick et al. |
| 5,868,757 A | | 2/1999 | Koutrouvelis |
| 5,871,448 A | | 2/1999 | Ellard |
| 5,906,574 A | | 5/1999 | Kan |
| 5,927,351 A | | 7/1999 | Zhu et al. |
| 5,928,130 A | | 7/1999 | Schmidt |
| 5,931,786 A | | 8/1999 | Whitmore |
| 5,938,583 A | | 8/1999 | Grimm |
| 5,957,935 A | | 9/1999 | Brown |
| 5,961,527 A | | 10/1999 | Whitemore |
| 6,007,474 A | | 12/1999 | Rydell |
| 6,010,446 A | | 1/2000 | Grimm |
| 6,036,632 A | | 3/2000 | Whitmore |
| 6,048,300 A | | 4/2000 | Thornton et al. |
| 6,102,844 A | | 8/2000 | Ravins |
| 6,106,455 A | | 8/2000 | Kan |
| 6,113,529 A | | 9/2000 | Shi |
| 6,129,670 A | | 10/2000 | Burdette |
| 6,241,706 B1 | | 6/2001 | Leschinsky et al. |
| 6,245,008 B1 | | 6/2001 | Leschinsky et al. |
| 6,258,056 B1 | * | 7/2001 | Turley et al. .................. 604/62 |

OTHER PUBLICATIONS

Website print–out: *Seed Plan Pro*, Oct. 1999.
Website print–out: *Seed Vac*, Oct. 1999.
Brochure: *Brachytherapy Source Calibration*, Standard Imaging, Middleton, Wisconsin, 8 pgs.; not dated.
Web Site print–out: Source Holders information, Standard Imaging, Middleton, Wisconsin, 2 pgs.; copyright 1998.
Web Site print–out: *Brachytherapy Product Directory*, Med–Tec, Inc., Orange City, Iowa, 1 pg.; Mar. 31, 2001.
Brochure: *HDR 1000 Plus—Ionization Chamber*, Standard Imaging, Middleton, Wisconsin, 15 pgs.; Feb. 15, 2000.

* cited by examiner

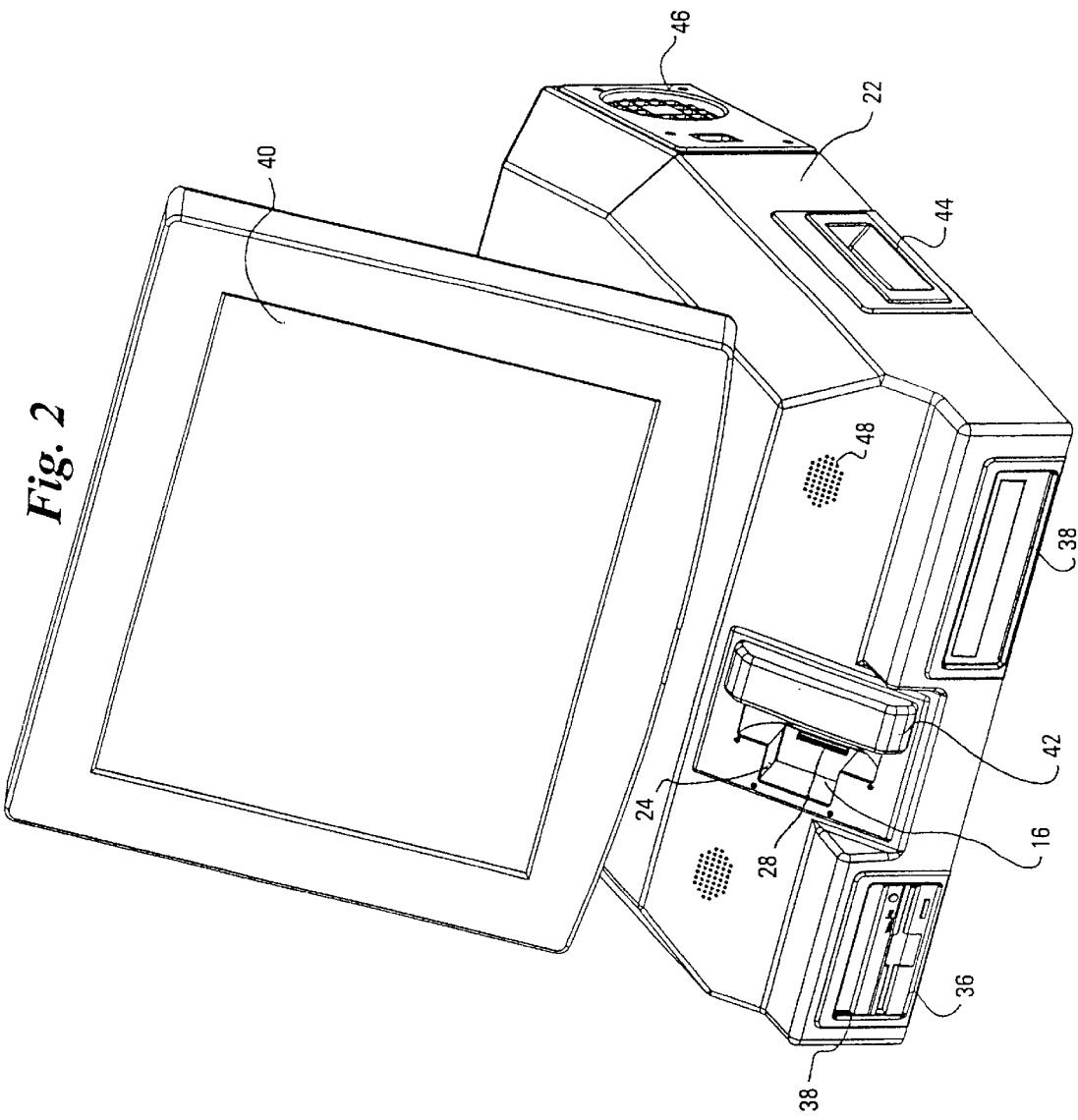

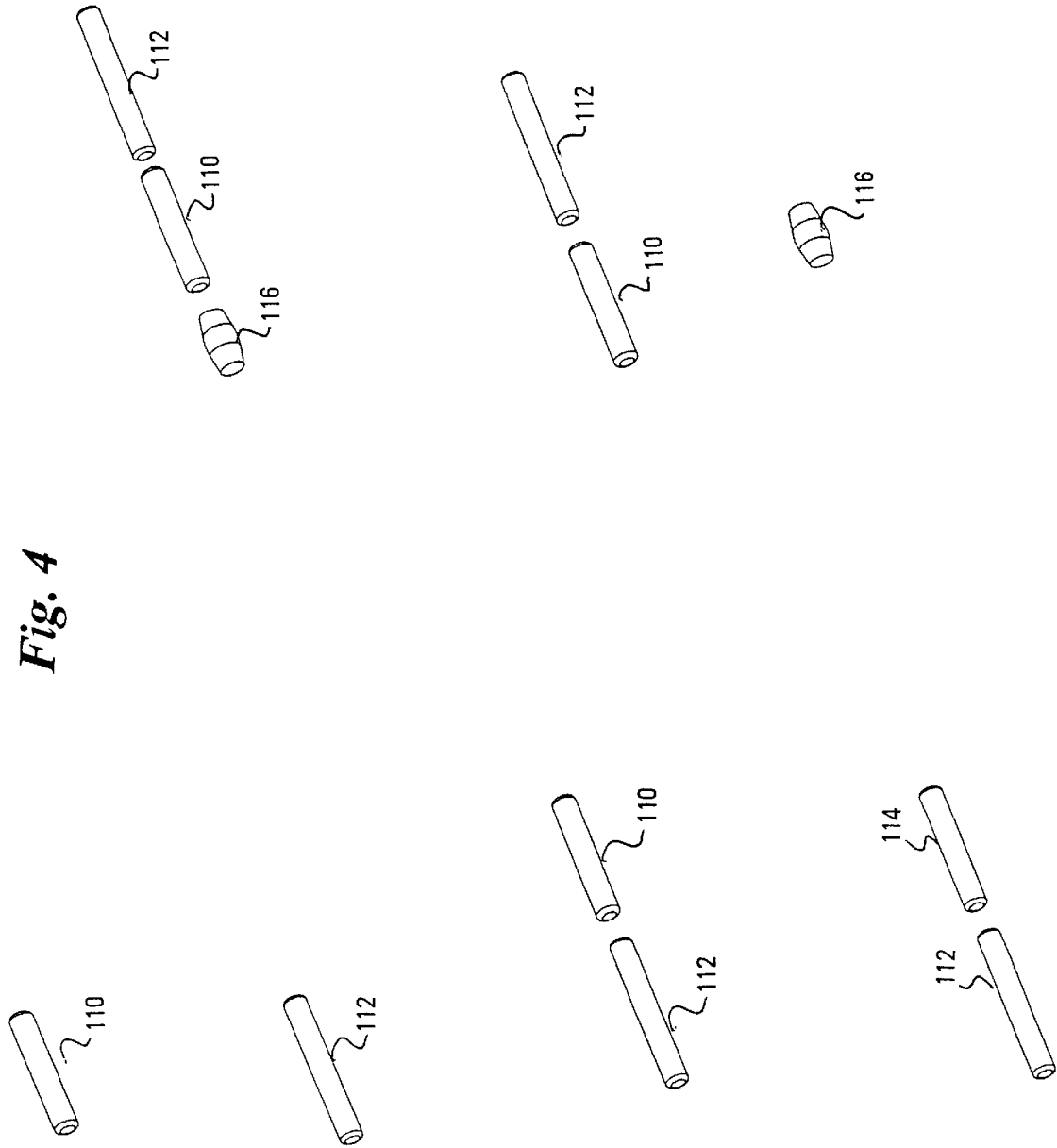

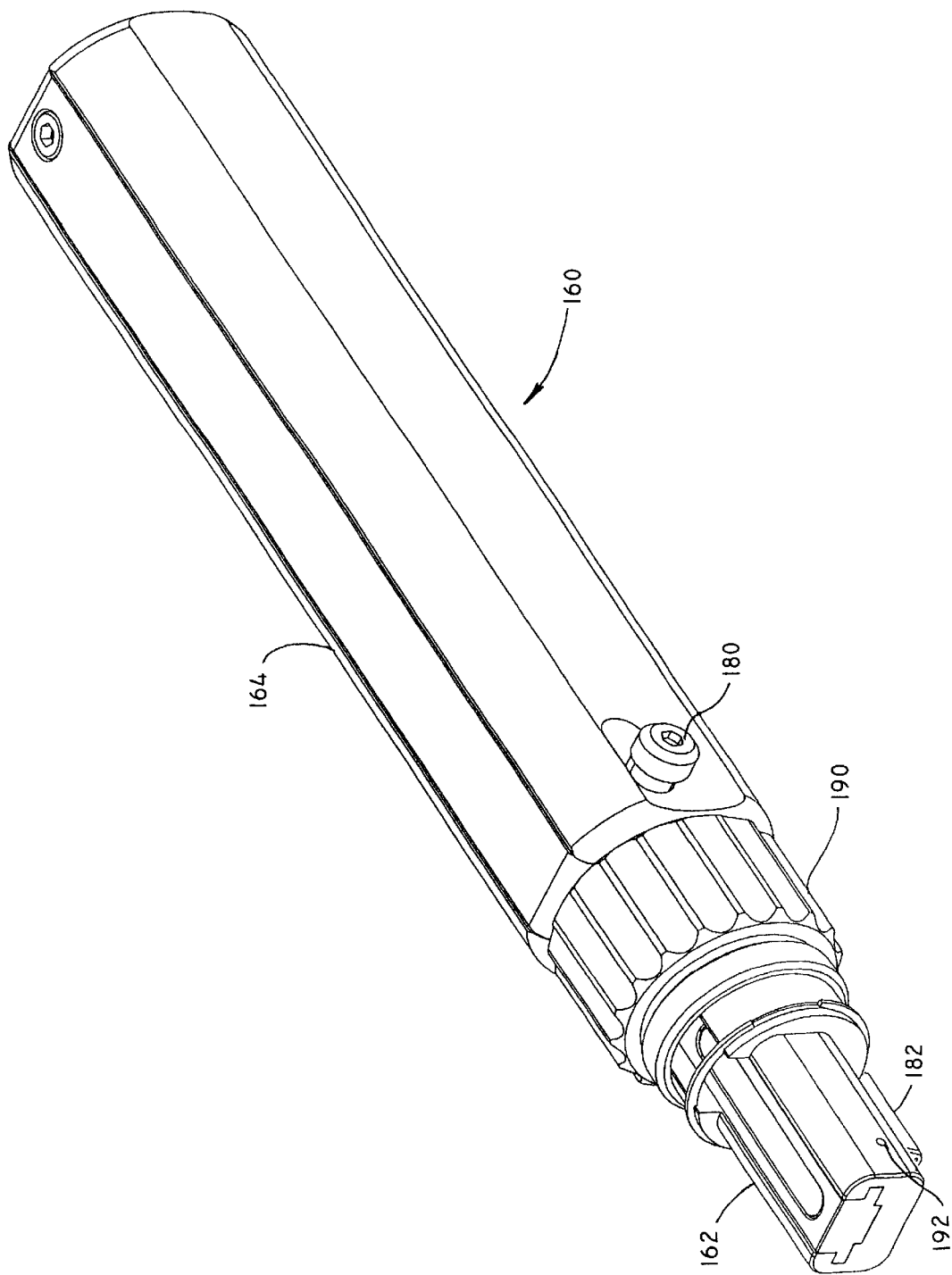

LOADING CLIP FOR RADIOISOTOPE SEEDS

RELATED APPLICATION

The present invention is a divisional of a co-pending application that is commonly assigned to the assignee of the present invention and entitled "AUTOMATED RADIOISOTOPE SEED CARTRIDGE," Ser. No. 09/587,642, filed Jun. 5, 2000, the disclosure of which is incorporated by reference. The present invention is related to a co-pending application that is commonly assigned to the assignee of the present invention and filed concurrently herewith, and is entitled "AUTOMATED RADIOISOTOPE SEED LOADER SYSTEM FOR IMPLANT NEEDLES," Ser. No. 09/587,624, filed Jun. 5, 2000, the disclosure of which is incorporated by reference.

FIELD OF THE INVENTION

The present invention relates generally to the field of medical devices for handling radioisotope materials. More specifically, the present invention relates to a loading clip for handling low dose radioisotope seeds for use in brachytherapy procedures or the like.

BACKGROUND OF THE INVENTION

The use of radioisotopes for various medical procedures such as brachytherapy and the like is well known. Such uses fall into two general categories: (i) high dose radioisotopes which are temporarily positioned in relation to a patient's body for a relatively short period of time to effect the radiation treatment, and (ii) low dose radioisotopes which are permanently implanted in a patient's body with the duration of the radiation treatment determined by the strength and half-life of the radioisotope being implanted. High dose radioisotopes are typically implanted using a catheter arrangement and a device commonly known as an afterloader that advances the high dose radioisotope located on the end of a source wire through the catheter to the desired location. Low dose radioisotopes, on the other hand, are implanted using an array of implant needles with the low dose radioisotopes being encapsulated in very small containers known as seeds that are manually loaded into a series of implant needles and then ejected to form a three-dimensional grid of radioisotopes in the patient that corresponds to a dose plan as determined by the physician. The goal of the low dose brachytherapy procedure is to position this three-dimensional grid of radioisotopes seeds in and around a target cancerous tissue area. Each of the radioisotope seeds consists of a radioactive source such as Iodine (I-125) or Palladium (Pd-103) inside a small tube-like titanium shell that is about the size of a grain of rice. These type of low dose radioactive sources emit a very low energy radiation that is primarily absorbed by the tissue immediately surrounding the radioisotope seed. This constant low energy radiation is typically emitted by the radioisotope seeds for a period of up to six months as a way to kill the cancer cells in the target area without having to subject the patient to the discomfort and risks that often accompany high dose radioisotope procedures.

One common brachytherapy procedure is the use of low dose radioisotopes to treat prostate cancer. Although brachytherapy procedures using low dose radioisotopes can be applied to many different parts of the body, it is helpful to describe a particular treatment to gain a better understanding of these treatments. In a typical prostate cancer procedure, a predetermined number of seeds (between 1–6) are positioned within each of a series of implant needles (up to 40), with the seeds being spaced apart in each needle by small spacers. A small amount of bone wax is positioned on the tip of the implant needles to prevent the seeds and spacers from falling out until they are implanted in the patient. The loaded implant needles are then positioned at the appropriate location for insertion into the perineal area of the patient using a stand that has an X-Y coordinate grid. Each needle is manually positioned in the appropriate chamber in the grid and is inserted into the patient. An ultrasound probe is used to assist the physician in guiding each of the needles to the desired location. The seeds and spacers are delivered from the tip of the implant needle using a stylet and hollow needle arrangement where the hollow needle is preferably retracted while the stylet remains in place. When completed, the implanted seeds form a three-dimensional grid of radioisotope sources that implements a predetermined dose plan for treating the prostate cancer in the patient. For a more detailed background of the procedures and equipment used in this type of prostate cancer treatment, reference is made to U.S. Pat. No. 4,167,179.

Over the years there have been numerous advancements in the design of equipment for use in radioisotope procedures. U.S. Pat. Nos. 4,150,298, 5,147,282, 5,851,172 and 6,048,300 describe replaceable cartridge assemblies that contain the source wire used in conjunction with specifically adapted afterloaders that advance the source wire into a catheter systems for high dose radioisotope procedures. U.S. Pat. No. 4,759,345 describes a shielded loading assemblies for hand implanted hypodermic needles. U.S. Pat. Nos. 4,815,449 and 4,763,642 describe a seed carrier that prepositions and encases a series of seeds in a body absorbable material. U.S. Pat. No. 5,906,574 describes a vacuum-assisted apparatus for manually handling and loading radioisotope seeds within a visible radiation shield. The same company which provides the vacuum-assisted apparatus described in U.S. Pat. No. 5,906,574, also provides an Indigo™ express seeding cartridge that is a tube with seeds prepositioned in the tube such that the tube accurately indexes and positions individual seeds in the well chamber of a radiation detector for purposes of calibrating the radioisotope seeds.

U.S. Pat. Nos. 4,086,914, 5,242,373 and 5,860,909, as well as PCT Publ. No. WO 97/22379, describe manual seed injector arrangements for a low dose radioisotope procedure that utilize drop-in seed cartridges or seed magazines to supply the seeds directly to an implant needle arrangement that is specifically adapted to such cartridges or magazines. U.S. Pat. Nos. 4,086,914, 5,242,373 and PCT Publ. No. WO 97/22379 describe seed cartridges in which the radioisotope seeds are maintained in an end-to-end relation to each other within the cartridge. The cartridge is positioned in an aligned, colinear relation with the bore of a needle and a manual push rod arrangement is used to eject the seeds from the cartridge. In U.S. Pat. No. 5,860,909, the cartridge is mounted above a magazine arrangement of an implant needle where the radioisotope seeds are maintained in a stacked side-by-side relation to each other within the cartridge. As a new seed is to be implanted, the bottom seed of the stack is released into the magazine and then ejected from the needle.

Although such replaceable cartridges have been well received for use in connection with high dose radioisotope procedures, the standard techniques for low dose radioisotope procedures continue to utilize a series of preloaded implant needles that are manually loaded by a radiophysicist at the hospital just prior to the procedure. There are several reasons for why manual loading of the implant needles just prior to use in low dose radioisotope procedures is preferred. First, there are differences in the types of radioisotope sources that do not favor use of a cartridge arrangement for low dose radioisotope procedures. The source wires used for high dose radioisotope procedures use only one or a small number of very high power radioisotope sources having relatively long half-lives. As a result, it is cost effective and practical to provide for a cartridge arrangement for such a small number of high dose radioisotopes that can be preordered and maintained at the hospital well in advance of a procedure. In contrast, given the relatively short half-lives of the radioisotopes used in low dose radioisotope procedures it is preferable that the radioisotope seeds be sent to the hospitals by overnight delivery for use the next day. Because the number of radioisotope seeds varies from procedure to procedure depending upon the dose plan and because the cost of each low dose radioisotope seed is significant, it is not cost effective to order more radioisotope seeds than will be used in a given procedure. Second, it is important to minimize the time of the procedure, both in terms of the exposure time of the physician to the low dose radioisotope seeds and in terms of the total time of the procedure from the economics of medical practice. The existing drop-in cartridge and seed magazine systems described above take longer to perform the implant procedure than using conventional preloaded implant needles because the radioisotope seeds are implanted one-by-one, rather than being delivered simultaneously as a group from a preloaded needle. Third, it has been routine to employ a radiophysicist at the hospital to preload the implant needles and take a set of sample measurements of the strength of the radioisotope seeds to confirm that the seeds meet the requirements specified by the dose plan. Finally, due to the large number of low dose radioisotope seeds used in a given procedure (typically up to 150) and the need for the implanting physician to be able to modify the dose plan at the time of implant, it is generally considered that the flexibility afforded by manually loading the implant needles just prior to the operation provides the best possible treatment procedure for the patient and the most economically efficient procedure for the hospital.

Although manual preloading of implant needles at the hospital continues to be the norm for most low dose radioisotope procedures, relatively little attention has been paid to increasing the safety or efficiency of this process. Presently, the radioisotope seeds for a given dose plan are shipped in bulk in a protective container by overnight delivery to the hospital. At the hospital, the radioisotope seeds are dumped from the container onto a tray where the radiophysicist manually loads the seeds one-by-one into a set of implant needles according to the dose plan. Typically, the implant needles are positioned tip into a needle stand with the tips sealed with bone wax. The radiophysicist picks up a single radioisotope seed using a tweezers, forceps or vacuum hose and deposits that seed in a needle. Next, a single spacer made of gut or similar absorbable material is deposited in the needle. This process is repeated depending upon the predetermined number of seeds and spacers prescribed by the dose plan. The radiophysicist will use a well chamber to measure the strength of a sample of the radioisotope seeds (typically from only one seed to a sample of about 10%). While some needle stands are provided with a certain degree of shielding once the radioisotope seeds are loaded in the implant needles, there is very little shielding that protects the hands and fingers of the radiophysicist during the process of manually loading the implant needles.

Despite the various attempts to improve this process, the handling of radioisotope seeds for low dose radioisotope procedures remains a cumbersome process that can expose radiophysicists, physicians and other hospital personal to unshielded radioisotopes. It would be advantageous to provide a loading clip for handling low dose radioisotope seeds for use in low dose radioisotope procedures that could overcome these problems and enhance the safety and efficiency of this process.

SUMMARY OF THE INVENTION

The present invention is a loading clip for low dose radioisotope seeds. The loading clip has a body having a channel defined therein. The channel has a cavity adapted for receiving a radioisotope seed at a distal end. A slider member slidably positionable within the channel has a spring biased tooth at a distal end. A constant force spring member is slidably positioned within the channel between the slider member and the body. Radioisotope seeds are magazined into the loading clip biased against the constant force spring member by operation of the slider member extending the tooth over the cavity and retracting a radioisotope seed in the cavity into the channel.

In one embodiment, radioisotope seeds are magazined into the loading clip that is then used to load an automated seed cartridge. In this embodiment, the loading clip has structure for mating with an aperture in the automated seed cartridge (referred to as the second aperture) so as to introduce radioisotope seeds into the second aperture one at a time. Preferably, the loading clip is provided with a machine readable storage medium accessible via an electrical connector that stores indicia representing at least information about the radioisotope seeds located in the loading clip. This information can be accessed by the automated cartridge system to automatically indicate information about the radioisotope seeds in the loading clip.

The automated cartridge for this embodiment has a housing that contains a selectively positionable member having a plurality of radioisotope seeds preloaded in chambers defined in the positionable member. A first aperture in the housing allows an elongated member to selectively eject radioisotope seeds from chambers in the positionable member when a given chamber is aligned with the first aperture. A mechanism in the cartridge automatically positions the selectively positionable member in alignment with the first aperture. Preferably, a feedback mechanism generates a positional feedback signal of a position of the chambers of the positionable member relative to the first aperture. The automated cartridge includes a second aperture rearward of the selectively positionable member along the line of travel of the elongated member through which at least radioisotope seeds are introduced into the line of travel of the elongated member and loaded into the chambers in the selectively positionable member via the loading clip.

A method of loading radioisotope seeds into an automated cartridge for use in an automated system for low dose radioisotope procedures is also disclosed. A replaceable cartridge is loaded into the automated system. The replaceable cartridge has a positionable member containing structure defining chambers for a plurality of radioisotope seeds and a housing arrangement having defined therein a first aperture through which an elongated member selectively ejects radioisotope seeds from chambers along a line of travel and a second aperture rearward of the positionable member along the line of travel of the elongated member through which radioisotope seeds are introduced into the line of travel of the elongated member and loaded into the chambers in the selectively positionable member. A separate loading clip in which a plurality of radioisotope seeds have been preloaded is operably connected to the second aperture of the replaceable cartridge. The radioisotope seeds are then automatically loaded into the selected chamber from the loading clip using the elongated member.

BRIEF DESCRIPTION OF THE DRAWINGS

FIG. 2 is a perspective of the automated system of FIG. 1 with an enclosure and showing the receiving structure that mates with the replaceable cartridge of the preferred embodiment of the present invention.

FIG. 4 is a schematic representation of the various combinations of radioisotope seeds, spacers and plugs as stored in the rotatable drum of the preferred embodiment of the replaceable cartridge of FIG. 3.

FIG. 11 is a perspective view of an assembled loading clip of FIG. 10.

DETAILED DESCRIPTION OF THE PREFERRED EMBODIMENT

Figure 1A:
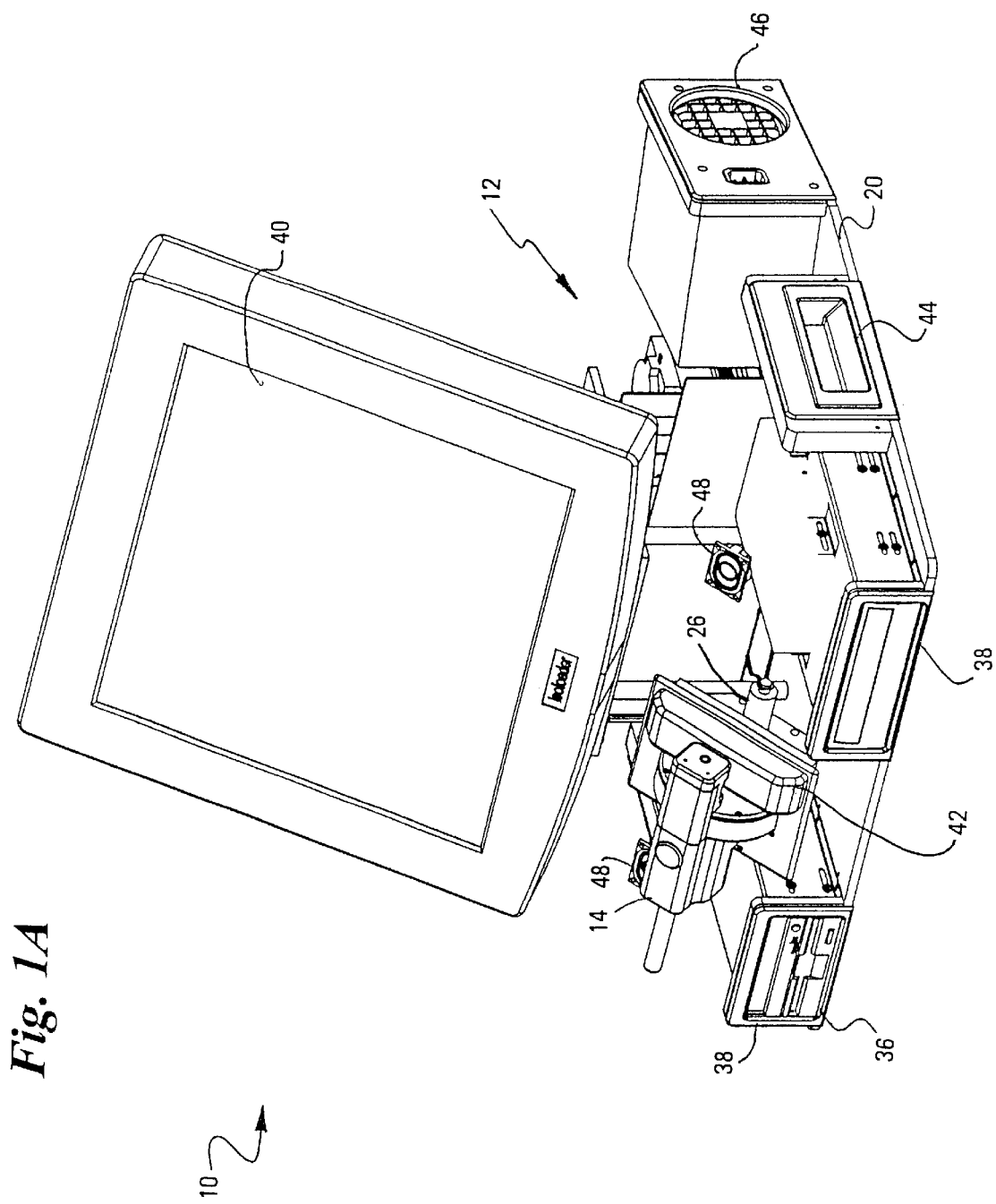
FIGS. 1A and 1B are perspective views of a preferred embodiment of the automated system for loading low dose radioisotope seeds and showing the preferred embodiment of the replaceable cartridge of the present invention in place within the automated loading system.
Figure 1B:
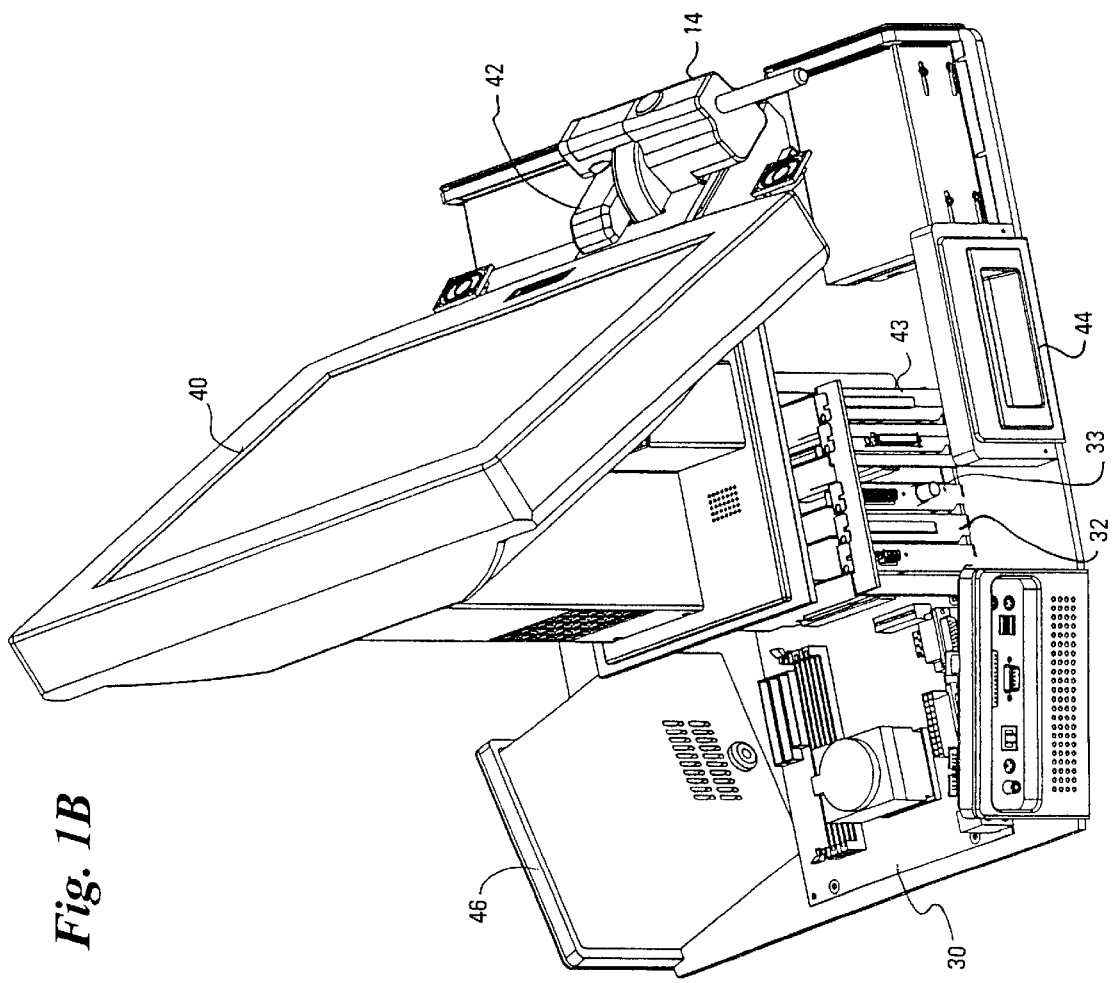

Referring to FIG. 1, an automated system 10 for loading low dose radioisotope seeds into a plurality of implant needles is comprised of a loading station 12 into which a replaceable cartridge 14 may be positioned. Preferably, the loading station 12 includes structure defining a cartridge receiving structure 16 in a front side of the loading station oriented toward a user as shown in FIG. 2. In this embodiment, the loading station 12 presents a front side toward a user with a corresponding longer dimension of the replaceable cartridge positioned in the cartridge receiving structure 16 parallel to this front side. Alternatively, the cartridge 14 and cartridge receiving structure 16 could be oriented transverse to the front side of loading station 12 or even at a rear side of loading station 12.

The loading station 12 has a base 20 (as shown in FIG. 1) and a cover 22 (as shown in FIG. 2) preferably formed of molded plastic or metal. A computer processor 30 for the automated system is preferably a motherboard having a microprocessor, internal bus, a PCI-compatible bus, DRAM and EPROM or battery backed SRAM, with appropriate external interfaces or mated PC boards for a video interface, multiple channel IDE interfaces, a floppy disk interface, an ethernet interface, COM and LPT interfaces, an external bidirectional parallel port and a serial port. An automated motion control system 32 is preferably a Galil motion controller available from Galil Motion Control Inc. that interfaces to the computer processor 30 via the PCI-compatible bus. The automated motion control system 32 with appropriate software drivers provides all functionality for the lowest level control of stepper motor position and feedback sensors. A hard disc drive 34, floppy disk drive 36, high density removable media drive 37 and CD or CD-RW drive 38 are also provided for storing data and information to be used by the automated system 10. A video display 40 which operates as the primary user interface is preferably a 1280 by 1024 resolution flat 18.1 inch flat panel LCD with a resistive touch screen, such as are available from National Display Systems. Alternatively, a conventional non-touch screen video display and mouse, keyboard or similar input devices could also be provided. A proportional counter type radiation sensor 42 is positioned to be able to sense the passage of radioisotope seeds from the cartridge 14 into the implant needles and verify the radiation strength of the radioisotope seeds. In the preferred embodiment, the radiation sensor 42 is connected to a multi-channel analyzer card 43 that serves as a data acquisition device for information from this sensor. For clarity, none of the interconnections or cables among the various elements are shown in FIG. 1. FIG. 2 shows one of a pair of handles 44 for carrying the loading station 12 and one of two fan units 46 for cooling the circuitry and components of the loading station 12. Speakers 48 are also included in the front of the loading station 12.

Referring specifically to FIG. 2, the downwardly angled cartridge receiving structure 16 of the preferred embodiment will be described. The cartridge receiving structure 16 includes an angled channel 24 with sides that define a downwardly angled path of travel for inserting at a preferred angle of approximately 45 degrees. Once in position, the loading station 12 locks the cartridge in place using an electrical solenoid 26 to prevent inadvertent removal of the cartridge 14 during operation of the automated system 10. Locking is initiated automatically once the presence of a cartridge 14 has been detected in the cartridge receiving structure 16 and the user has initiated a loading operation via display 40. Unlocking the cartridge is initiated by the user selecting a remove cartridge operation via display 40, but only after computer processor 30 has confirmed completion of any critical motions that are part of the needle loading operation and removed power to the cartridge 14. Preferably, the only other interface between the cartridge 14 and the cartridge receiving structure 16 is a multiple pin-type electrical connector 28. As the stepper motors and associated encoder discs are contained within the cartridge 14, the need for extremely tight tolerance matches between the channel 24 of the cartridge receiving structure 16 and the cartridge 14 is minimized. In addition to the necessary control and sensor signals, the connector 28 include a ground and power connection to provide power to the cartridge 14. The presence of cartridge 14 in cartridge receiving structure 16 is also detected via a contact on connector 28. Although an angled channel 24 is the preferred embodiment for interfacing the cartridge 14 with the cartridge receiving structure 16, it will be recognized that many other structures, such as guide rails, latches, pivoting arrangements, ball and detent locks, and orientations, such as horizontal or vertical, and connectors, such as optical, infrared, RF, slide contacts, array contacts or the like, could be used to accomplish the same function of interfacing the cartridge 14 with the cartridge receiving structure 16.

For a more detailed description of the preferred embodiment of the automated system 10 and its preferred, operation and user interface, reference is made to the previously identified co-pending application entitled "AUTOMATED RADIOISOTOPE SEED LOADER SYSTEM FOR IMPLANT NEEDLES."

Figure 3A:
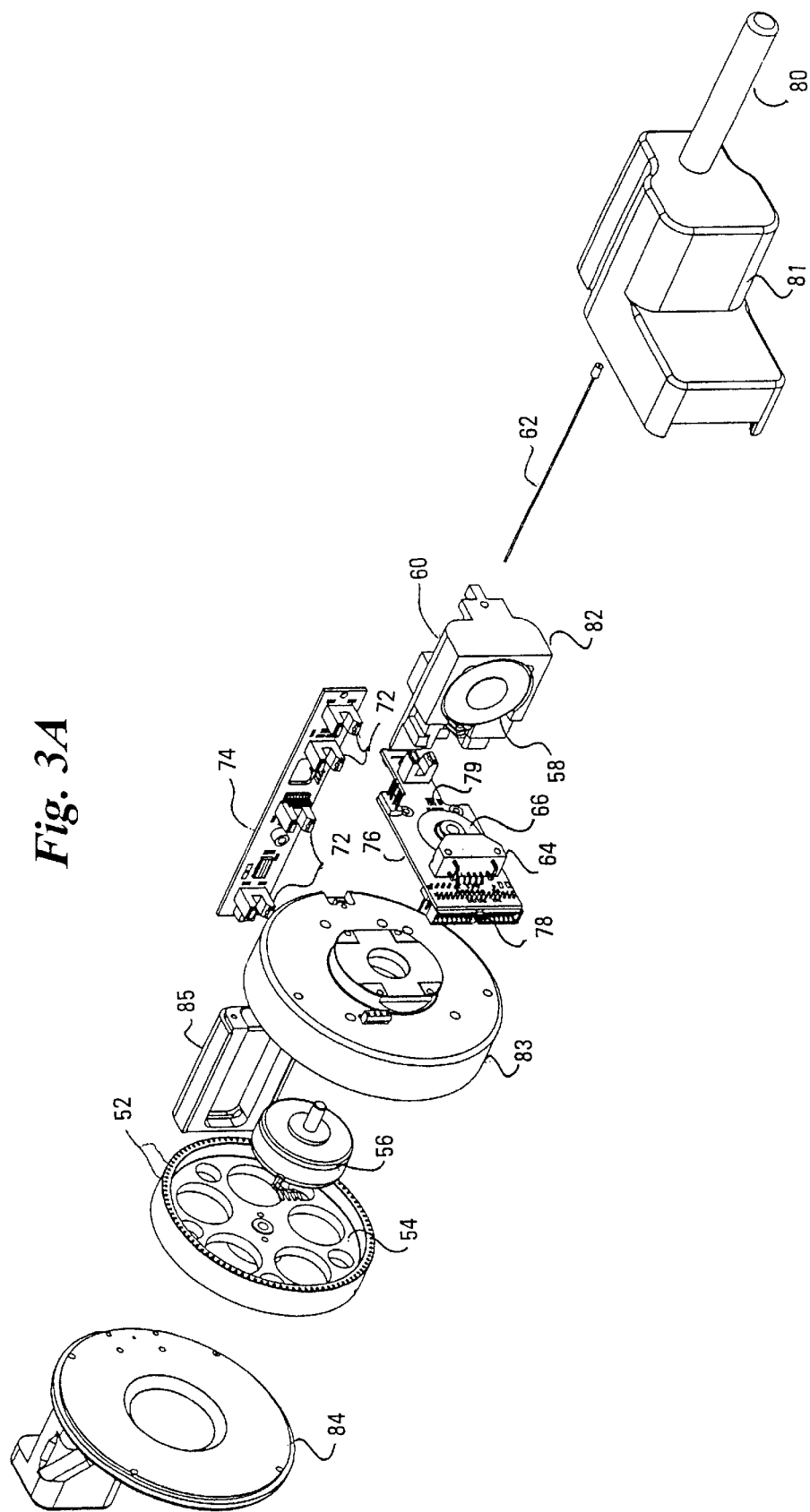
FIGS. 3A and 3B are exploded perspective views of the preferred embodiment of the replaceable cartridge of FIG. 1 that loads needles from the rear.
Figure 3B:
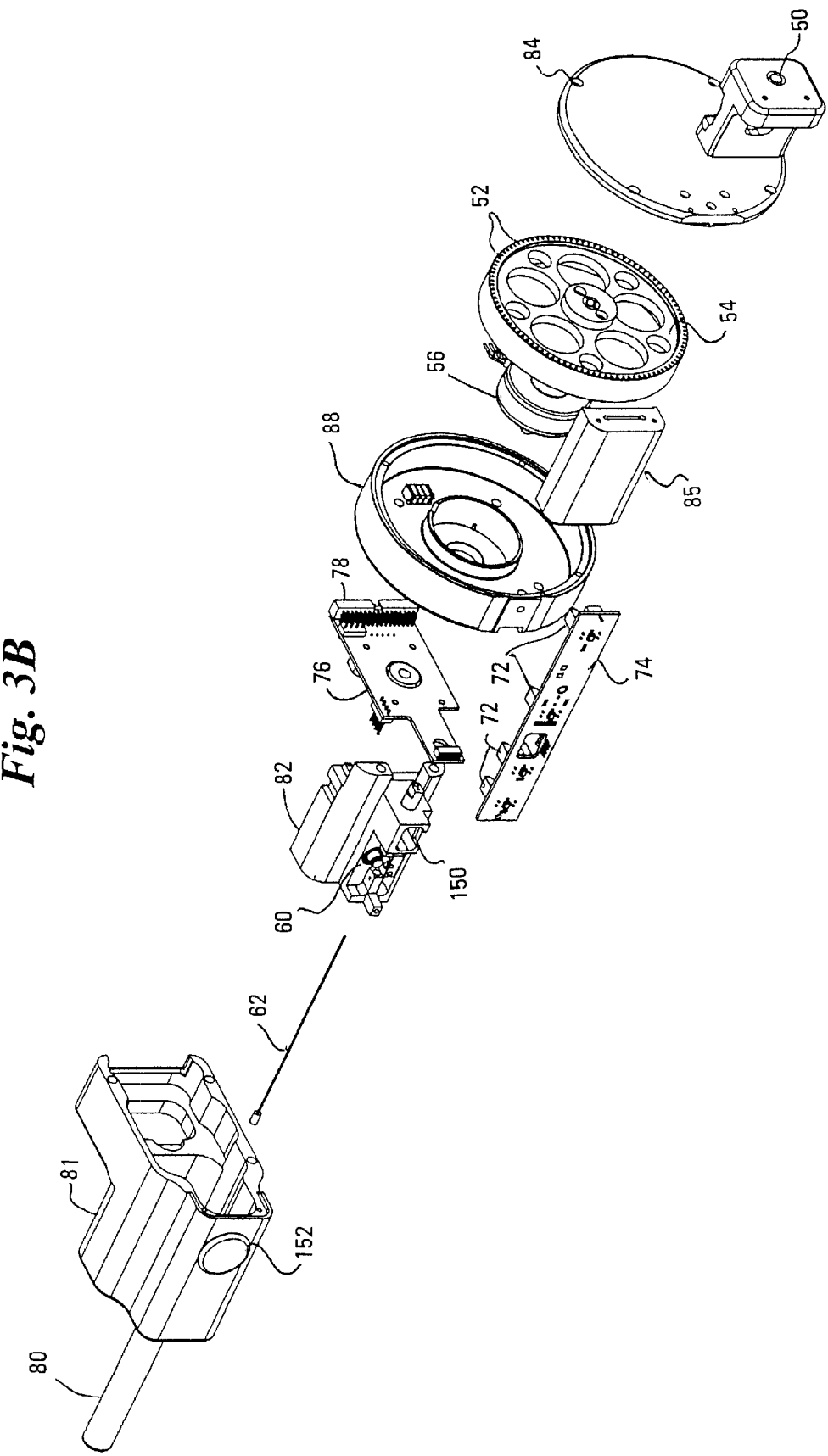

Referring now to FIGS. 3A and 3B, the cartridge 14 contains a plurality of radioisotope seeds and a plurality of spacers preloaded into the cartridge. The cartridge 14 has at least one aperture 50 into which an implant needle is positioned. Preferably, the radioisotope seeds and spacers are loaded into holes or chambers 52 located around the periphery of a rotatable drum 54. In this embodiment, the cartridge 14 includes a pair of stepper motors within the cartridge. A first stepper motor 56 rotates the rotatable drum 54. It will be seen that stepper motor 56 preferably drives rotatable drum 54 directly without any intervening gearing arrangement. A second stepper motor 58 has a capstan assembly 60 that rotates in engagement with a push rod 62 to slide the push rod 62. For the rotatable drum 54, an encoder detector 64 detects the position of a corresponding encoder disc 66 which is then communicated back to automated motion control system 32 (FIG. 1). Preferably, the stepper motor and encoder are selected such that the stepper motor steps in full steps with relation to the distance between chambers around the periphery. The alignment of the aperture to the chambers in the drum is preferably initially accomplished at the time of assembly. It will also be seen that other motor drives other than stepper motors could be used with equivalent success in the present invention, such as servo motors, worm driven motors, or DC motors with appropriate indexing control.

Figure 7:
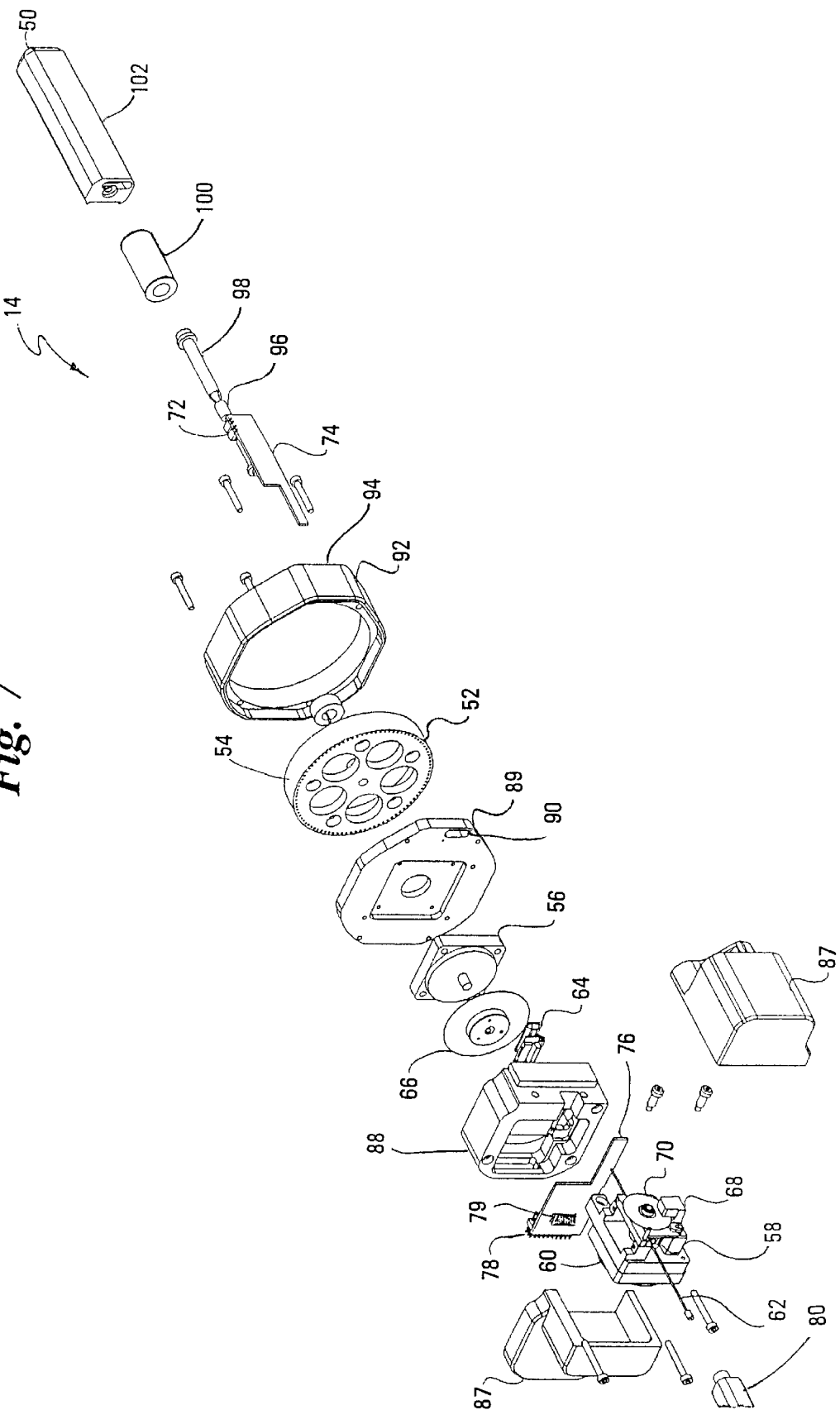
FIG. 7 is an exploded perspective view of an alternative embodiment of the replaceable cartridge that loads needles from the tip.

In an alternative embodiment as shown in FIG. 7, an encoder with a higher degree of resolution can be used and the stepper motor can be incremented in less than full steps. In this embodiment, a first encoder for the rotatable drum generates a positional feedback signal of an index of the chambers of the rotatable drum relative to the line of travel of the linear actuator 60, and a second encoder 68 with a second encoder disc 70 for the linear actuator 60 that generates a positional feedback signal of a position of the elongated member along the line of travel.

Referring again to FIG. 3, a series of position sensors 72 are positioned in line with the push rod 62 to detect the travel of push rod 62 as it is driven by capstan system 60 through its line of travel. The sensors 72 are connected to sensor circuitry 74 to communicate this position information to the automated motion control system 32. Each of the encoder detector 64 and sensor circuitry 74 are electrically-connected to a circuit board 76 which has an appropriate connector 78 for mating with and connecting with a corresponding connector 28 (FIG. 2) in the cartridge receiving structure 16 of the housing 12.

Preferably, the circuit board 76 is provided with an electrically eraseable programmable read-only memory (EEPROM) 79 or similar non-volatile memory to store parameters and other data that are unique to the particular cartridge 14 and to the particular patient and dose plan that has been developed for that patient. The contents of EEPROM 79 are set up initially during loading and calibration of the cartridge 14 at the factory. These contents are updated by the automated system 10 so as to continually reflect the current state of the cartridge 14. For example, when the radioisotope seeds and/or spacers are ejected from a given chamber 52, then the data on the EEPROM 104 is updated to reflect that the given chamber 52 no longer contains any radioisotope seeds and/or spacers. Preferably, the EEPROM 79 is capable of storing patient and hospital identification information, as well as seed inventory and manufacture information. Optionally, the EEPROM could also store the predetermined dose plan for the particular patient.

In the preferred embodiment, various housing elements enclose the cartridge 14 to create a single, enclosed drop-in cartridge to simplify operation and handling of the cartridge as shown in FIG. 3. Preferably, the various housing elements are formed of machined stainless steel to enhance the protective aspect of the housing. Alternatively, the housing could be formed of materials other than stainless steel. For example, the housing elements could be molded plastic with appropriate pieces having an internal lead lining or the like to provide sufficient shielding. Although the preferred embodiment is described as a single, enclosed drop-in cartridge, it will be understood by those skilled in the art that some or all of the functional components of cartridge 14 may be separately enclosed or left unenclosed and operably connected together to accomplish the same functionality, such as allowing for mating with the cartridge receiving structure 16 and protecting movement of the push rod 62 along its line of travel.

In the preferred embodiment of the rear loading cartridge 14 as shown in FIG. 3, a push rod sleeve 80 encloses the travel of push rod 62. Cover 81 is a one piece unit that covers the capstan assembly 60 and its associated components. A capstan motor mount 82 provides a mounting base for most of the main components of cartridge 14, including circuit board 76 and encoder detector 64. Housing 83 houses the stepper motor 56 and the rotatable drum 54. A cover plate 84 mounts to the housing plate 83. The motor mount 82 and the cover 81 are secured by internal screws (not shown) that are accessed when the cover plate 84 is removed. A front plate 85 covers the circuit board 74 and is also mounted with screws between cover plate 84 and cover 81. A needle housing 86 is also screwed on to the cover plate 84 and includes the aperture 50 through which the needle accesses the cartridge.

Figure 6:
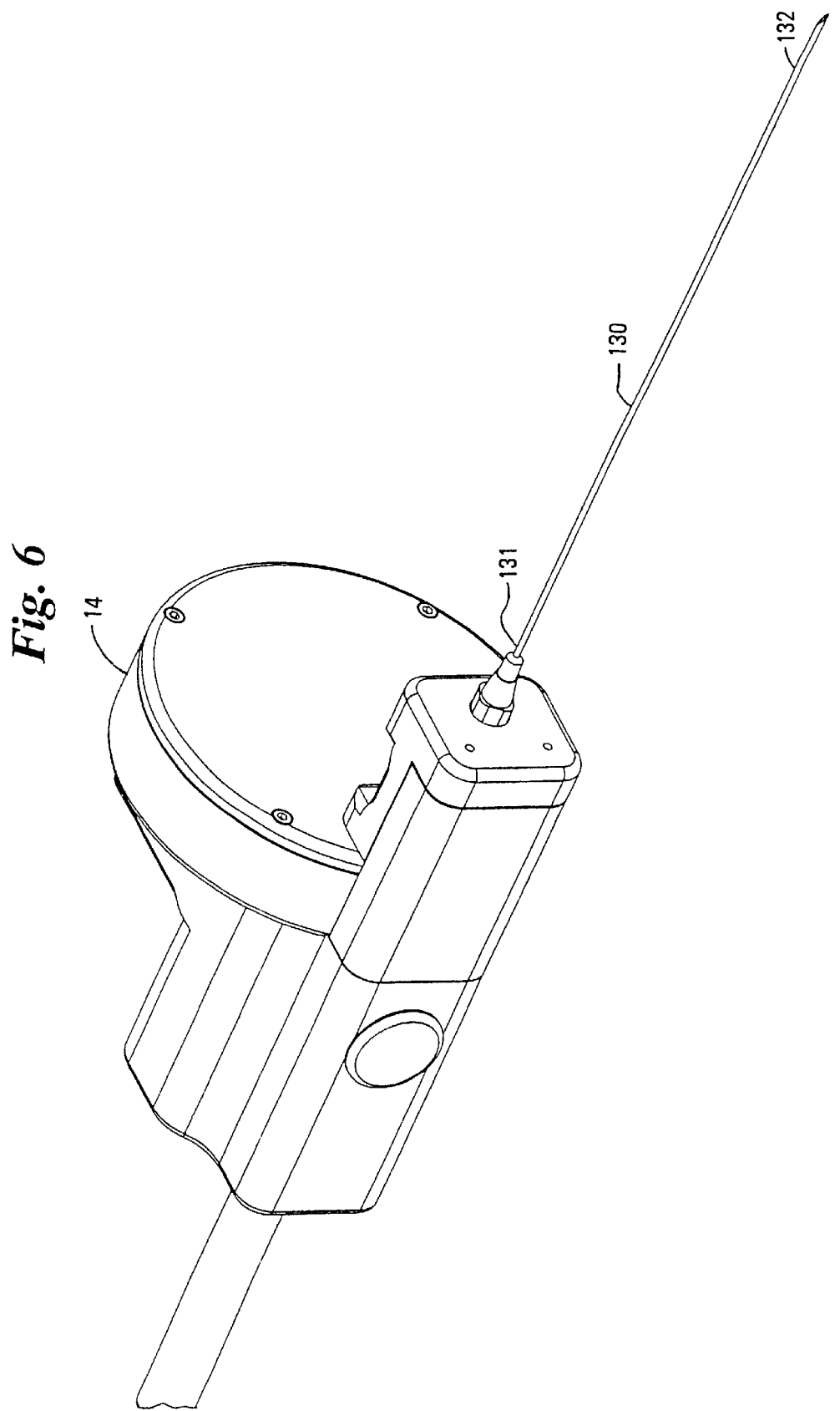
FIG. 6 is a perspective of the assembled replaceable cartridge of FIG. 3 with a needle to be loaded from the rear.

In the preferred embodiment as shown in FIG. 6, the contents are loaded into the rear 131 of the implant needle 130 which has its tip 132 plugged with bone wax or a similar plug material. Alternatively, a crimp at the tip 132 could prevent the contents of chamber from being pushed out the tip 132 of the needle 132 as it is loaded from the rear 131. In this embodiment, the rear 131 of the needle 130 is preferably secured in place in the aperture 50 by a Luer lock or similar assembly. Preferably, the tip 132 does not extend beyond the side of loading station 12 as a safety measure.

Figure 9:
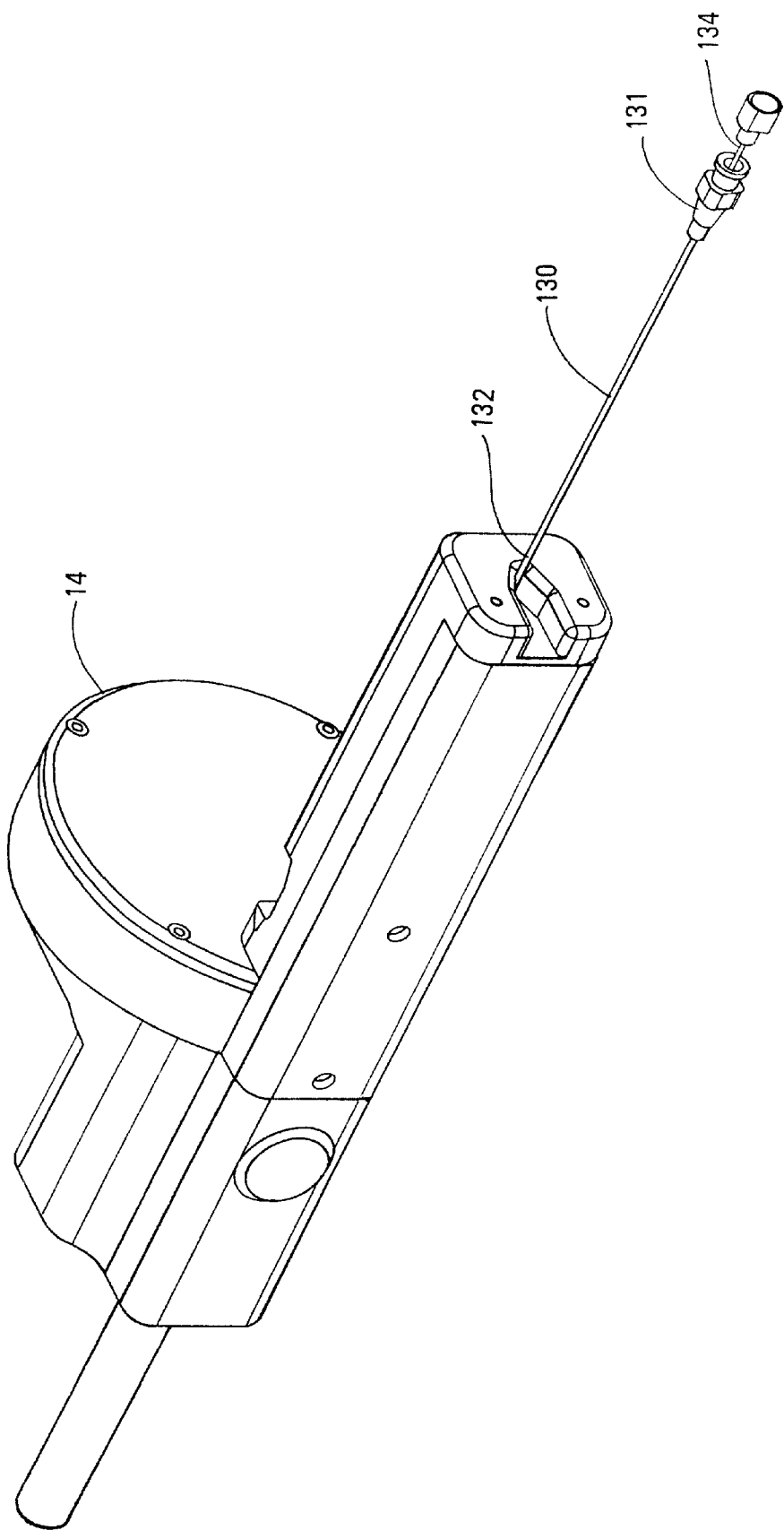
FIG. 9 is a perspective view of an assembled replaceable cartridge with a needle to be loaded from the tip.

In an alternate embodiment as shown in FIGS. 7 and 9, the contents are loaded into the tip 132 of the needle 130, rather than into the rear 131 of the needle 130. In this embodiment, the housing elements are configured somewhat differently than in the rear loading embodiment. A rod sleeve 80 encloses the travel of push rod 62. Housing halves 87 mate to abase 88 to cover the capstan assembly/linear actuator 60 and its associated components. The base 88 provides a mounting base for most of the main components of cartridge 14 of the tip loading embodiment, including circuit board 76 and encoder detector 64. Plate 89 provides a mounting structure for stepper motor 56 and includes an aperture 90 through which push rod 62 slides to engage the radioisotope seeds and spacers located in the chambers 52 around the periphery of rotatable drum 54. Plate 89 also prevents radioisotope seeds and spacers from falling out of the chambers 52 on one side of rotatable drum 54. A cap-like cover 92 is mounted over the other side of rotatable drum 54 and includes an aperture 94 by which access is provided to sensor circuitry 74 and through which push rod 62 slides to eject the radioisotope seeds and spacers into the implant needle (not shown) via an alignment tube 96. An alignment structure 98 preferably comprising a beveled alignment needle guide has an internal channel that aligns a corresponding beveled implant needle with the alignment tube 96. An electrical solenoid 100 is used to lock the implant needle in place relative to the cartridge 14 once the proper positioning of the implant needle in the alignment structure 98 has been confirmed. In the this embodiment, the at least one aperture 50 is defined on an end of a shield tube 102 constructed of appropriate metal to shield the radioisotopes as they are being loaded into the implant needle.

In addition to the advantages afforded by constructing cartridge 14 as a single, enclosed drop-in cartridge, the preferred embodiment of cartridge 14 is designed with minimum piece parts to allow for easy disassembly and sterilization to allow for potential re-use. Once the various covers and circuit assemblies are removed, the remaining portions of cartridge 14 are cleaned with alcohol or hydrogen peroxide to remove bioburden. When reassembled, the entire cartridge 14 is preferably sterilized with a gas sterilization technique. The ease of disassembly also provides a convenient mechanism by which emergency removal of the radioisotope seeds can be accomplished, simply be removing cover 92 and dumping the radioisotope seeds and spacers into an appropriate container.

The use of a rotatable drum 54 also affords important advantages to the preferred embodiment of the present invention. The positioning of the chambers 52 around the periphery of drum 54 reduces the concentration of radiation sources at any given point and provides an optimum separation of radioisotope seeds from each other, thereby enhancing the safety of cartridge 14.

In the preferred embodiment, each chamber 52 is long enough to accommodate any of a combinatorial set of radioisotope seeds, spacers and plugs. As shown in FIG. 4, various combinations of radioisotope seeds 110, full-length spacers 112, partial-length spacers 114 which can serve as blanks and plugs 116 can be positioned within a given chamber 52. In this embodiment, the length of one radioisotope seed 110 or one blank 114 is 4.5 mm, the length of one full length spacer 112 is 5.5 mm and the length of one plug 116 is 2 mm. As will be apparent, the selection of the lengths of each of the seeds 110, spacers 112, 114 and plugs 116 allows for various combinations to be utilized that have the same overall length when positioned in an implant needle of 10 mm for seed and spacer or 12 mm for seed, spacer and plug. The particular combination of each for a given cartridge is optimally determined at the time that the cartridge 14 is preloaded in accordance with a predetermined dose plan. This information can then be utilized by the automated station 10 to load the implant needles in accordance with that predetermined dose plan.

In the preferred embodiment, the rotatable drum 54 is provided with 200 chambers 52 spaced equidistant about the periphery of the rotatable drum 54. The optical encoder disc 66 preferably has 400 or 1600 lines of resolutions which yields a resolution of 2 or 8 counts per chamber 52. In an alternate embodiment with higher resolution as previously described, 72,000 lines of resolution are used which yields a resolution of 360 counts per chamber 52. A home reference is provided by an index channel on the encoder disc 66. The alignment of the aperture 50 to the chambers 52 in the drum 54 using the index channel is preferably accomplished at the time of assembly. In the high resolution embodiment, an offset to a first chamber location clockwise from the home reference is stored as a parameter for the cartridge 14 to allow for individual cartridge tolerance calibration. Alternatively, an optical sensor could be used to locate the center of a chamber 52 for purposes of calibrating an index. In operation, the automated motion control system 32 uses the stepper motor 56 and encoder circuitry 64 to establish a reference to the first seed drum chamber 52. Motion of the drum 54 may take place bidirectionally (i.e., clockwise or counterclockwise) and as rapidly as possible in order to move to the nearest desired chamber location as determined by the computer processor 30 and automated motion control system 32 in the shortest possible time. When requested by the computer processor 30, the automated motion control system 32 will index to the center of the desired chamber location in preparation for transfer of the contents of that chamber 52 to the implant needle. The drum 54 will remain at this location until it is commanded to a new position.

Figure 5:
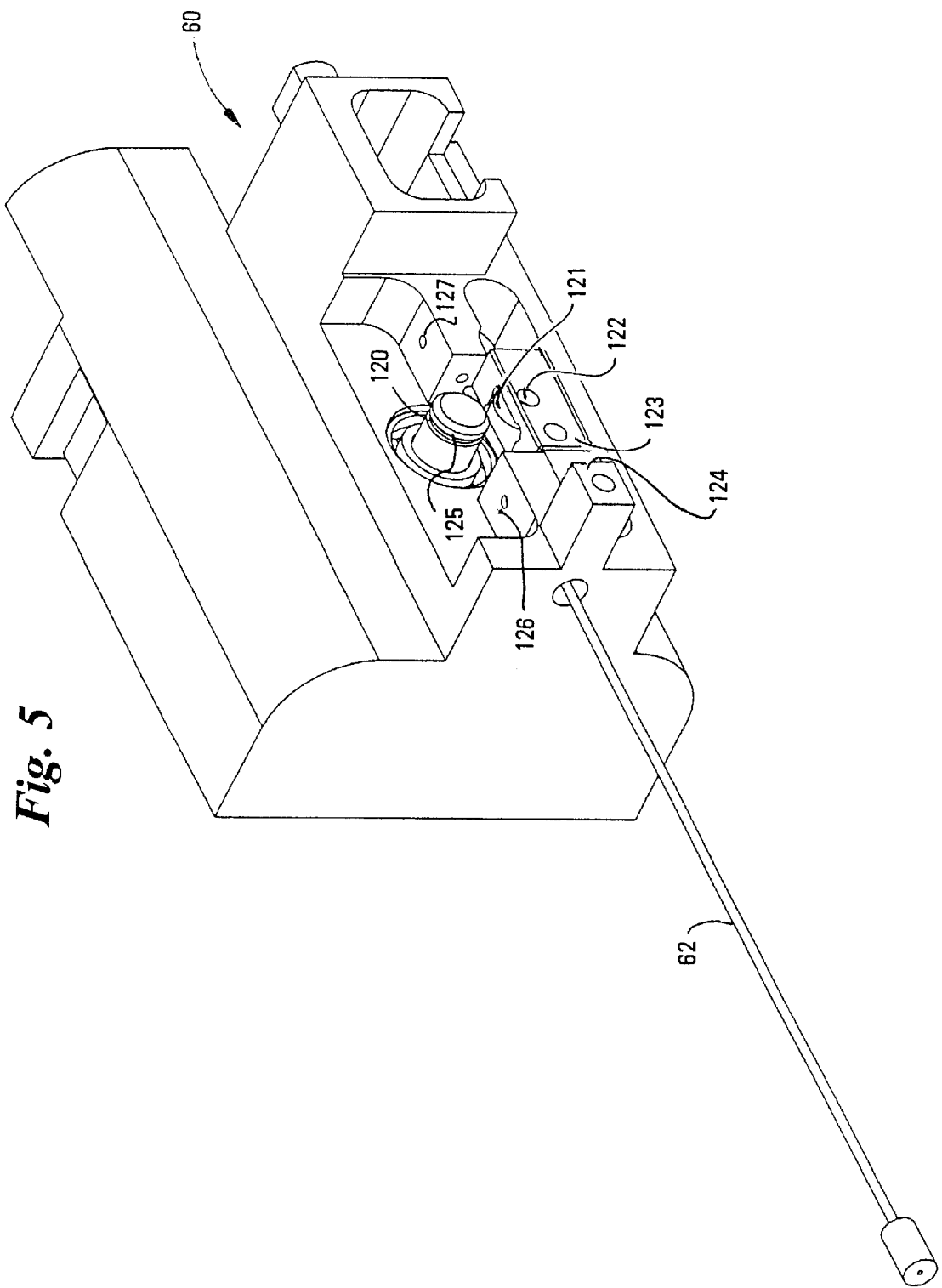
FIG. 5 is a detailed view of a capstan assembly for the push rod of the preferred embodiment of the replaceable cartridge of FIG. 3.

Referring now to FIG. 5, a preferred embodiment of the capstan assembly 60 will be described. A pair of capstans 120, 121 are positioned above and below the line of travel of push rod 62. The upper capstan 120 is preferably the shaft of stepper motor 58. The lower capstan 121 is preferably a ball bearing 122 held in a biased pivot arm 123 biased by a spring 124. Preferably, the upper capstan 120 includes a radial channel 125 adapted to guide the push rod 62. The pivot arm 123 pivots back to allow the push rod 62 to enter the capstan assembly 60. Once engaged, the channel 125 guides the push rod 62 as it is frictionally held between capstans 120, 121. In the preferred embodiment, the channel 125 is aligned with respect to the chambers 52 by adjusting the motor 58 that drives the capstan assembly 60 to the desired depth. A positive travel limit is preferably established using a first optical sensor 126 that is part of the structure of capstan assembly 60 which detects the back of the push rod 62 passing through a defined point. A negative travel limit for the line of travel of push rod 62 is established by a second optical sensor 127 that doubles as a home reference. Preferably, the travel limits do not disable the stepper motor 58, but rather send an indication to the automated motion control system 32 that the respective travel limit has been exceeded. Once zeroed in relation to the home reference, the push rod 62 is moved forward and into an open chamber 52 in the drum 54. This serves as a loose mechanical lock to prevent the drum 54 from being rotated unintentionally. When a request for a seed transfer is generated by the computer processor 30, the automated motion control system 32 activates the capstan assembly 60 to retract the push rod 62, thereby allowing the drum 54 to be rotated freely.

When the drum 54 has been indexed to the desired chamber location, the automated motion control system 32 instructs the stepper motor 58 to move the push rod 62 forward to push the contents of the chamber 52 out of the drum 54 and into the tube 96 leading to the radiation sensor 42. The distance the push rod will travel will be based on the total length of the contents in the given chamber and the location of the radiation sensor 42. Because the automated motion control system 32 knows the nature of the contents of each chamber 52, the push rod would be instructed to stop and position the radioisotope seed in front of the radiation sensor 42 if a radioisotope seed was present in the contents of a given chamber and if the computer processor 30 determined that a radiation measurement should be acquired based upon the radiation sensing parameters as set by the user of the automated system 10. In this case, a message would be communicated from the automated motion control system 32 to the computer processor 30 when the radioisotope seed 110 was properly positioned indicating that a radiation measurement may be performed. Once a radiation measurement has been taken, or if no radiation measurement is required, the automated motion control system instructs the stepper motor 58 to move the push rod 62 forward to deliver the contents into the implant needle 130.

The trailing one of the position sensors 72 is provided along the path of material transfer to allow for detection of the leading edge of the contents with relation to the tip of push rod 62. As the contents of a given chamber 52 are moved by the position sensor 72, the total length of the contents may be determined. This allows for a verification of the length of the contents of a given chamber 52 with the information the automated system has about what should be in that chamber 52 to prevent potential misloads. In the event of an early or late activation of the sensor 72 by the tip of the push rod 62 in relation to the expected activation based on the anticipated length of the contents of that given chamber 52, an alarm or error message would be passed to the computer processor 30.

In the tip loading embodiment as shown in FIG. 9, as the contents are delivered into the implant needle 130, a stylet 134 that is preferably positioned in the implant needle 130 is pushed back by the advancing contents. In this way the needle 130 and stylet 134 are ready to use as soon as the loading process is completed and it is not necessary to insert a stylet into the implant needle after the loading process is completed, thereby incurring the risk that the stylet would dislodge the plug 116 or displace any of the loaded contents from the implant needle 130.

As any given implant needle 130 may be loaded from the contents of one or more chambers 52, it is important that the contents of a given chamber 52 containing a plug to be inserted at the tip 132 of implant needle 130 be accurately aligned with the end of the tip 132. In this case, the automated motion control system 32 preferably moves the contents of the chamber 52 containing a plug to an absolute location relative to the tip 132 of the implant needle 130, rather than moving the contents a relative distance based on the expected lengths of the contents of that chamber. In this way, the plugs 116 are always inserted so that they are flush with the ends of the tips 132 of the implant needles 130.

Figure 8:
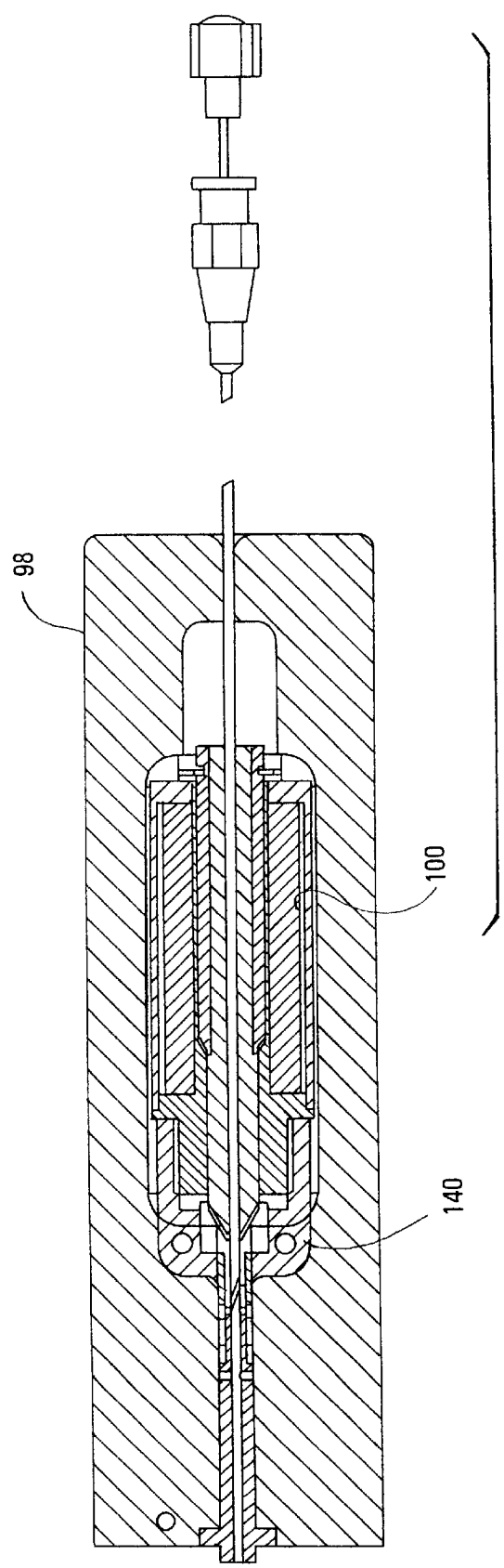
FIG. 8 is a detailed cross-sectional view of a tip alignment structure, radiation sensor and needle sensing system of the replaceable cartridge of FIG. 9.

Referring now to FIG. 8, an embodiment of the alignment structure 98 and the positioning of an implant needle 130 will be described. In order to begin a loading cycle, the needle tip 132 must be properly positioned by the user so that a known location is established for the needle tip 132. An optical sensor 140 is positioned precisely at the desired location of the needle tip 132 and is connected to the sensor circuitry 74 (FIG. 1). Preferably, the alignment structure 98 is beveled to match a beveling on the tip 132 of the implant needle 130. To accomplish proper alignment, the user inserts the implant needle 130 into the aperture 50 until it abuts alignment structure 98 and then rotates the implant needle 130 until the optical sensor 140 indicates proper alignment. Preferably, the optical sensor 140 remains active during the loading process to confirm that there is no movement of implant needle 130 during this process. Once the proper positioning of the implant needle 130 has been confirmed, an electrical solenoid 100 is activated to clamp the implant needle 130 in place relative to the cartridge 14. The force of the solenoid 100 is such that the implant needle 130 may not be moved during the loading operation, but not sufficient to crush the implant needle 130. In the preferred embodiment, the solenoid 100 is automatically released once the loading of the implant needle 130 is complete and a plug 116 has been inserted into the tip 132 of the implant needle 130.

Figure 10:
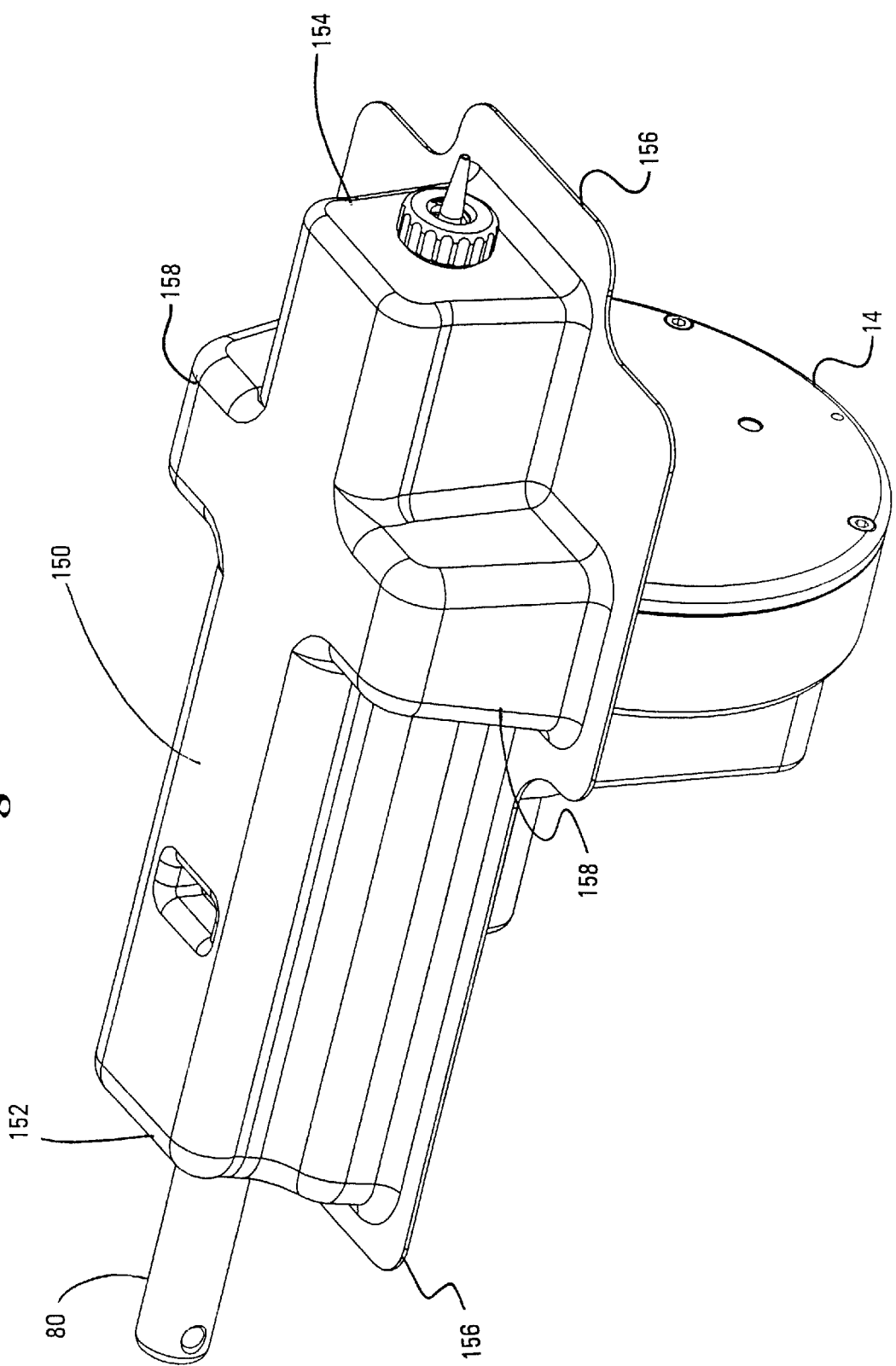
FIG. 10 is an exploded perspective view of a preferred embodiment of a loading clip in accordance with the present invention.

Referring now to FIGS. 10 and 11, the embodiment of the present invention that includes a loading clip 160 will now be described. In one embodiment, the automated cartridge 14 can be preloaded at a factory and shipped for usage with radioisotope seeds inside. In another embodiment the automated cartridge 14 includes a second aperture 150 rearward of the rotatable drum 54 along the line of travel of the push rod 62 through which radioisotope seeds are introduced into replaceable cartridge 14. Preferably, the second aperture 150 is covered by a loading clip cap 152 and includes screw based structure 154 or the like for securing the loading clip 160 onto the cartridge 14. As the seeds are loaded from the loading clip 160 into the replaceable cartridge 14, the push rod 62 is controlled to load the seeds one at a time into the chambers 52 in the drum 54. The loading clip 160 has structure 162 for mating with the second aperture 150 to introduce radioisotope seeds into the second aperture 150 one at a time.

Preferably, the loading clip 160 has a body 164 having a channel 166 defined therein, the channel 166 having a cavity 168 adapted for receiving a radioisotope seed at a distal end. A slider member 170 is slidably positioned within the channel 166 has a spring biased tooth 172 at a distal end. A spring 174 biases the slider member 170 toward the distal end of the body 164. A constant force spring member 176 is slidably positioned within the channel 166 between the slider member 170 and the body 164. A cover 178 secures the components within the channel 166. Radioisotope seeds are magazined into the loading clip 160 biased against the constant force spring member 176 by operation of a handle 180 on the slider member 170 which extends the tooth 172 over the cavity 168 and retracts a radioisotope seed in the cavity 168 into the channel 166. Preferably, the loading clip 160 is provided with a machine readable storage medium such as EEPROM 182 accessible via an electrical connector that stores indicia representing at least information about the radioisotope seeds located in the loading clip 160. A mating structure 190 preferably screws into the structure 154 on the cartridge 14.

In order to quickly load the loading clip 160, an aperture 192 near the cavity 168 parallel to the line of travel of the push rod 62 and parallel to the orientation of the channel 166 allows radioisotope seeds to be introduced into the cavity 168 as quickly as handle 180 can be activated. In one embodiment, this can be accomplished automatically under machine control of handle 180 and providing a continuous supply of radioisotope seeds connected to the aperture 192 in end-to-end fashion. Alternatively, the cavity 168 may be manually loaded with seeds one at a time using a tweezers, for example. In a preferred embodiment, the loading clip 160 is capable of loading up to sixty seeds and/or spacers. Preferably, one loading clip 160 will be loaded with seeds and a second loading clip 160 will be loaded with spacers. The computer processor 30 then loads the seeds from the first loading clip into the appropriate chambers 52 in the drum 54 in accordance with a predetermined dose plan. After the second loading clip 160 is mounted on the cartridge 14, the computer processor 30 directs the loading of the spacers into the appropriate chambers 52 in the drum 54 in accordance with a predetermined dose plan.

Although the cartridge 14 of the present invention has been described with respect to the automated station 10, it will be understood that the cartridge 14 of the present invention may also be used with other automated equipment as part of a low dose brachytherapy procedure. For example, the elongated member used to eject the radioisotope seeds in the preferred embodiment is a push rod 62 that loads the seeds into a plurality of implant needles. Where the cartridge 14 is used with an automated needle insertion system, the elongated member may be a trocar needle or similar cutting member that would first make an incision into the patient, then be withdrawn, and finally advanced through the aperture of the cartridge to eject the seeds.

Although the drum 64 has been described as the preferred embodiment of the positional member of the cartridge 14 with its movement controlled by stepper motor 56, it should be understood that other forms of this positional member and other motor arrangements would also work within the scope of the present invention. For example, the positionable member could be an X-Y grid of chambers with a pair of stepper motors used to drive the grid in X-Y directions to position the desired chamber in line with the aperture and push rod. 62. Although stepper motors, such as stepper motor 56, and encoders, such as encoder 58 are a convenient and economical manner of implementing the present invention so that it may be controlled by an external microprocessor arrangement, it will be recognized that other arrangements such as gears, drive belts and clutched motor shafts could be used in place of the stepper motor, and that contact sensors, optical sensors or registry from a known starting point could also be used in place of the encoder. It will also be seen that while the preferred embodiment interfaces with an external microprocessor, it would also be possible to incorporate a microprocessor into the cartridge itself and to communicate externally by telecommunications, radio communications or the like, instead of by electrical connectors.

What is claimed is:

1. A loading clip for low dose radioisotope seeds, comprising:

a body having a channel defined therein, the channel having a cavity adapted for receiving a radioisotope seed at a distal end;

a slider member slidably positionable within the channel having a spring-biased tooth at a distal end;

a constant-force spring member slidably positionable within the channel between the slider member and the body, such that radioisotope seeds are magazined into the loading clip biased against the constant-force spring member by operation of the slider member extending the tooth over the cavity and retracting a radioisotope seed in the cavity into the channel; and a machine-readable storage medium in the loading clip accessible via an electrical connector that stores indicia representing at least information about the radioisotope seeds located in the loading clip.

2. The loading clip of claim 1 further comprising an aperture in the cavity orthogonal to the orientation of the channel whereby radioisotope seeds are introduced into the cavity.

3. A method of loading radioisotope seeds into an automated cartridge for use in an automated system for low dose radioisotope procedures comprising:

loading a replaceable cartridge into the automated system, the replaceable cartridge having a positionable member containing structure defining chambers for a plurality of radioisotope seeds and a housing arrangement having defined therein a first aperture through which an elongated member selectively ejects radioisotope seeds from chambers along a line of travel and a second aperture rearward of the positionable member along the line of travel of the elongated member through which radioisotope seeds are introduced into the line of travel of the elongated member and loaded into the chambers in the selectively positionable member;

operably connecting a separate loading clip to the second aperture of the replaceable cartridge, the loading clip having a plurality of radioisotope seeds preloaded therein; and automatically loading radioisotope seeds into the selected chamber from the loading clip using the elongated member.

4. The method of claim 3 further comprising:

automatically positioning the positionable member and generating a positional feedback signal of a position of the chambers relative to the line of travel such that radioisotope seeds are automatically loaded when the positional feedback signal indicates that a selected chamber is in line with the line of travel.

5. A system for loading an automated cartridge for use in an automated system for low dose radioisotope procedures, comprising:

a housing arrangement, the housing arrangement including structure that mates with structure of the automated system;

a selectively positionable member within the housing arrangement having structure defined therein for containing a plurality of radioisotope seeds in chambers defined in the positionable member;

a first machine-readable storage medium in the housing accessible via a first electrical connector that stores indicia representing a content of each chamber in the positionable member;

a first aperture in the housing arrangement through which an elongated member selectively ejects radioisotope seeds from chambers in the positionable member when a given chamber is aligned with the aperture along a line of travel of the elongated member;

a second aperture in the housing arrangement rearward of the selectively positionable member along the line of travel of the elongated member through which radioisotope seeds are introduced into the line of travel of the elongated member and loaded into the chambers in the selectively positionable member;

automated means for positioning the selectively positionable member; and a loading clip containing at least a plurality of radioisotope seeds and having structure for mating with the second aperture to introduce radioisotope seeds into the second aperture one at a time;

a second machine-readable storage medium in the loading clip accessible via a second electrical connector that stores indicia representing a content of the loading clip, such that information from the indicia in the second machine-readable storage medium is transferred to the first machine readable storage medium under control of the automated system.

6. A system for loading an automated cartridge for use in an automated system for low dose radioisotope procedures, comprising:

a housing arrangement, the housing arrangement including structure that mates with structure of the automated system;

a selectively positionable member within the housing arrangement having structure defined therein for containing a plurality of radioisotope seeds in chambers defined in the positionable member;

a first aperture in the housing arrangement through which an elongated member selectively ejects radioisotope seeds from chambers in the positionable member when a given chamber is aligned with the aperture along a line of travel of the elongated member;

a second aperture in the housing arrangement rearward of the selectively positionable member along the line of travel of the elongated member through which radioisotope seeds are introduced into the line of travel of the elongated member and loaded into the chambers in the selectively positionable member;

automated means for positioning the selectively positionable member; and a loading clip containing at least a plurality of radioisotope seeds and having structure for mating with the second aperture to introduce radioisotope seeds into the second aperture one at a time, the loading clip comprising:

a body having a channel defined therein, the channel having a cavity adapted for receiving a radioisotope seed at a distal end;

a slider member slidably positionable within the channel having a spring-biased tooth at a distal end; and a constant-force spring member slidably positionable within the channel between the slider member and the body, such that radioisotope seeds are magazined into the loading clip biased against the constant-force spring member by operation of the slider member extending the tooth over the cavity and retracting a radioisotope seed in the cavity into the channel.

7. The system of claim 6 further comprising an aperture in the cavity orthogonal to the orientation of the channel whereby radioisotope seeds are introduced into the cavity.

8. The system of claim 6 further comprising:

a machine readable storage medium in the loading clip accessible via an electrical connector that stores indicia representing at least information about the radioisotope seeds located in the loading clip.

* * * * *